(12) United States Patent
Wang et al.

(10) Patent No.: US 9,329,176 B2
(45) Date of Patent: May 3, 2016

(54) GLYCOPEPTIDE-FUNCTIONALIZED NANOPARTICLES ARRAYS FOR CAPTURING AND DETECTING BIOMOLECULES

(75) Inventors: Yuh-Lin Wang, Taipei (TW); Ting-Yu Liu, Hsinchu County (TW); Huai-Hsien Wang, Tainan County (TW)

(73) Assignee: Academia Sinica, Taipei (TW)

( * ) Notice: Subject to any disclaimer, the term of this patent is extended or adjusted under 35 U.S.C. 154(b) by 907 days.

(21) Appl. No.: 12/949,052

(22) Filed: Nov. 18, 2010

(65) Prior Publication Data
US 2012/0129707 A1    May 24, 2012

(51) Int. Cl.
| | |
|---|---|
| G01N 21/65 | (2006.01) |
| G01N 33/569 | (2006.01) |
| G01N 33/58 | (2006.01) |
| G01N 33/553 | (2006.01) |
| G01N 33/543 | (2006.01) |

(52) U.S. Cl.
CPC ........ G01N 33/54353 (2013.01); G01N 21/658 (2013.01); G01N 33/553 (2013.01); G01N 33/56911 (2013.01); G01N 33/587 (2013.01)

(58) Field of Classification Search
CPC ............. C40B 30/40; G01N 33/54353; G01N 21/658; G01N 33/56911; G01N 33/587; G01N 33/553
USPC .......................................................... 506/13
See application file for complete search history.

(56) References Cited

U.S. PATENT DOCUMENTS

| | | | |
|---|---|---|---|
| 2005/0105085 A1* | 5/2005 | Naya .............................. | 356/301 |
| 2006/0252065 A1 | 11/2006 | Zhao et al. | |
| 2009/0149344 A1 | 6/2009 | Zhao et al. | |
| 2009/0303472 A1 | 12/2009 | Zhao et al. | |
| 2011/0143332 A1* | 6/2011 | Lin et al. ......................... | 435/5 |

FOREIGN PATENT DOCUMENTS

EP       2063253       5/2009

OTHER PUBLICATIONS

Sarma et al., (Journal Biological Chemistry, 1971, vol. 246, No. 11, pp. 3753 to 3759).*
Avidin Biotin Handbook, Thermo Scientific, 2009, p. 3.*
Gu et al. (Chemical Communications, 2006, pp. 941-949, "Biofunctional magnetic nanoparticles for protein separation and pathogen detection").*
Schafer et al. (Structure, 1996, vol. 4, No. 12, pp. 1509-1515, "Crystal structure of vancomycin").*
Cui et al. (Antimicrobial Agents and Chemotherapy, 2006, vol. 50, No. 3, pp. 1079-1082, "Correlation between Reduced Daptomycin Susceptibility and Vancomycin Resistance in Vancomycin-Intermediate *Staphylococcus aureus*").*

(Continued)

*Primary Examiner* — Jeremy C Flinders
(74) *Attorney, Agent, or Firm* — Cesari and McKenna LLP

(57) ABSTRACT

A surface-enhanced Raman spectroscopic (SERS) system for detecting a biomolecule. The system includes a substrate, an array of nanoparticles disposed on the substrate, each being partially embedded in the substrate and having a non-embedded surface, and a linking agent disposed on the non-embedded surface of each of the nanoparticles. The array of nanoparticles has a uniform interparticle gap of 1-50 nm and the linking agent is capable of binding to the biomolecule.

20 Claims, 7 Drawing Sheets

(56) References Cited

OTHER PUBLICATIONS

Demirel et al. "Bio-organism sensing via surface enhanced raman spectroscopy on controlled metal/polymer nanostructured substrates" Biointerphases; 4(2):35-41 (2009).

Gu et al. "Presenting vancomycin on nanoparticles to enhance antimicrobial activities"; American Chemical Society; 3(9):1261-1263 (2003).

Gu et al. "Using biofunctional magnetic nanoparticles to capture vancomycin-resistant enterococci and other gram-positive bacteria at ultralow concentration" J. AM. Chem. Soc. 125:15702-15703 (2003).

Gu et at "Using biofunctional magnetic nanoparticles to capture gram-negative bacteria at an ultra-low concentration" Chem. Commun. 1966-1967 (2003).

Gao et al. "Combining fluorescent probes and biofunctional magnetic nanoparticles for rapid detection of bacteria in human blood" Adv. Mater.; 18:3145-3148 (2006).

Liu et al. "A high speed detection platform based on surface-enhanced raman scattering for monitoring antibiotic-induced chemical changes in bacteria cell wall" PLoS One 4(5):1-10 (2009).

Ndieyira et al. "Nanomechanical detection of antibiotic-mucopeptide binding in a model for superbug drug resistance"; Nature Nanotechnology; 3:691-696 (2008).

Wang et al. "Highly raman-enhancing substrates based on silver nanoparticle arrays with tunable sub-10 nm gaps"; Adv. Mater.; 18:491-495 (2006).

Williams et al. "The vanocycin group of antibiotics and the fight against resistant bacteria" Angew. Chem. Int. Ed.; 38:1172-1193 (1999).

Chattopadhyay, et al., "Surface-Enhanced Raman Spectroscopy Using Self-Assembled Silver Nanoparticles on Silicon Nanotips", Chem. Mater. 2005, 17, 553-559.

Liu, et al., "Functionalized arrays of Raman-enhancing nanoparticles for capture and culture-free analysis of bacteria in human blood", Nature Communications, Nov. 2011.

Tripp, et al., "Novel nanostructures for SERS biosensing", Nano Today, vol. 3, No. 3-4, 2008.

\* cited by examiner

GLYCOPEPTIDE-FUNCTIONALIZED NANOPARTICLES ARRAYS FOR CAPTURING AND DETECTING BIOMOLECULES

BACKGROUND OF THE INVENTION

Surface-enhanced Raman spectroscopy (SERS) has been employed for label-free analysis of microorganisms and biomolecules to exploit its $10^6$~$10^{10}$ times enhancement in the Raman signal.

A variety of SERS substrates have been prepared by, e.g., disposing colloidal metal nanoparticles on a surface, roughening a metal surfaces to possess nanometer-scale features, or creating nanostructures on a surface by lithography. See, e.g., Demirel, M. C. et al., *Biointerphases* 4, 35-41 (2009); Stern, E. et al., *Nature Nanotech.*, 5, 138-142 (2010); Nie, S. et al., *Science*, 275, 1102-1106 (1997); Fang, Y. et al., *Science*, 321, 388-392 (2008); Li, J. F. et al., *Nature*, 464, 392-395 (2010); Tripp, R. A. et al., *Nanotoday*, 3, 31-37 (2008); Kao, P. et al., *Adv. Mater.*, 20, 3562-3565 (2008); Shachaf, C. M., et al., *PLoS ONE*, 4, e5206-e5217 (2009); and Qian, X. et al., *Nature Biotechnol.*, 26, 83-90 (2008).

Yet, there is still great need to develop new SERS substrates suitable for detecting biomolecules or microorganisms in a rapid, reliable, and uniform manner.

SUMMARY OF THE INVENTION

This invention is based at least in part on the unexpected discovery that certain SERS substrates, when coated with certain compounds (e.g., a glycopeptide antibiotic such as vancomycin), exhibit uniformly high sensitivity enhancement in detecting a biomolecule (e.g., a peptide on the cell wall of a bacterium). Thus, this invention relates to a SERS system and their use.

One aspect of this invention relates to a surface-enhanced Raman spectroscopic (SERS) system for detecting a biomolecule. The system includes a substrate, an array of nanoparticles disposed on the substrate, each being partially embedded in the substrate and having a non-embedded surface, and a linking agent disposed on the non-embedded surface of each of the nanoparticles. The linking agent is capable of binding to the biomolecule, e.g., a peptide on the cell wall of a bacterium. The term "nanoparticle" refers to the nanostructure in the shape of a particle having a diameter in the range of 10 nm to 100 nm and an aspect ratio between 1 and 5 (e.g., between 1 and 3).

This system may include one or more of the following features:

The system features (i) a substrate surface containing an array of wells having a uniform inter-well gap of 1-50 nm (e.g., less than 10 nm) and (ii) an array of nanoparticles being disposed in the array of wells, each well containing one nanoparticle. The wells are formed of aluminum oxide, titanium oxide, tantalum oxide, or niobium oxide. The term "inter-well gap" refers to the shortest distance between the outer rims of two neighbouring wells.

The array of nanoparticles in the system is formed of Ag, Au, or Cu. The non-embedded surface of nanoparticles is also formed of Ag, Au, or Cu. The inter-nanoparticle gaps can be uniform and the shortest distance can be 1-50 nm between the outer surfaces of two neighboring nanoparticles.

The linking agent used in the system can be any one of following glycopeptide antibiotics: vancomycin, teicoplanin, ristocetin, televancin, bleomycin, ramoplanin, chloroeremomycin, and decaplanin. It is reversibly (e.g., non-covalently) attached to the non-embedded surface of each of the nanoparticles. Preferably, its molecular weight is not greater than 5 kDa, and, more preferably, not greater than 2 kDa. This linking agent forms, over the array of nanoparticles, a coating layer that has a thickness of 5-100 nm, e.g., 10-30 nm.

Another aspect of the present invention features a method for detecting the presence of a target biomolecule in a sample. The method includes providing a SERS system described above, contacting the SERS system with a sample suspected of containing the biomolecule, and detecting a SERS spectrum change (e.g., a change in the Raman spectrum shape or peak intensity) of the SERS system after the contacting step. When a SERS spectrum change is observed, it indicates that the sample contains the target biomolecule, which can be a peptide on the cell wall of a bacterium. This method may further include, after the detecting step, correlating a level of the SERS spectrum change with a concentration of the target biomolecule in the sample so as to quantify the target biomolecule. After the detecting step, the SERS system can be washed with a suitable solution to release the linking agent bound to the nanoparticles.

The details of several embodiments of the invention are set forth in the description below. Other features or advantages of the present invention will be apparent from the following drawings and actual examples, and also from the appended claims.

BRIEF DESCRIPTION OF THE DRAWINGS

The drawings are first described.

FIG. 5*a* illustrates the bacteria-capturing capability of various vancomycin-functionalized SERS substrates (coating solutions having 80 μM-50 mM of vancomycin; $10^9$ cfu/ml bacteria seeding concentration) while FIG. 5*b* illustrates the bacteria sensitivity of a vancomycin-functionalized SERS substrate (coating solution having 10 mM of vancomycin; various bacteria seeding concentrations of $10^3$-$10^9$ cfu/ml).

DETAILED DESCRIPTION OF THE INVENTION

Figure 1:
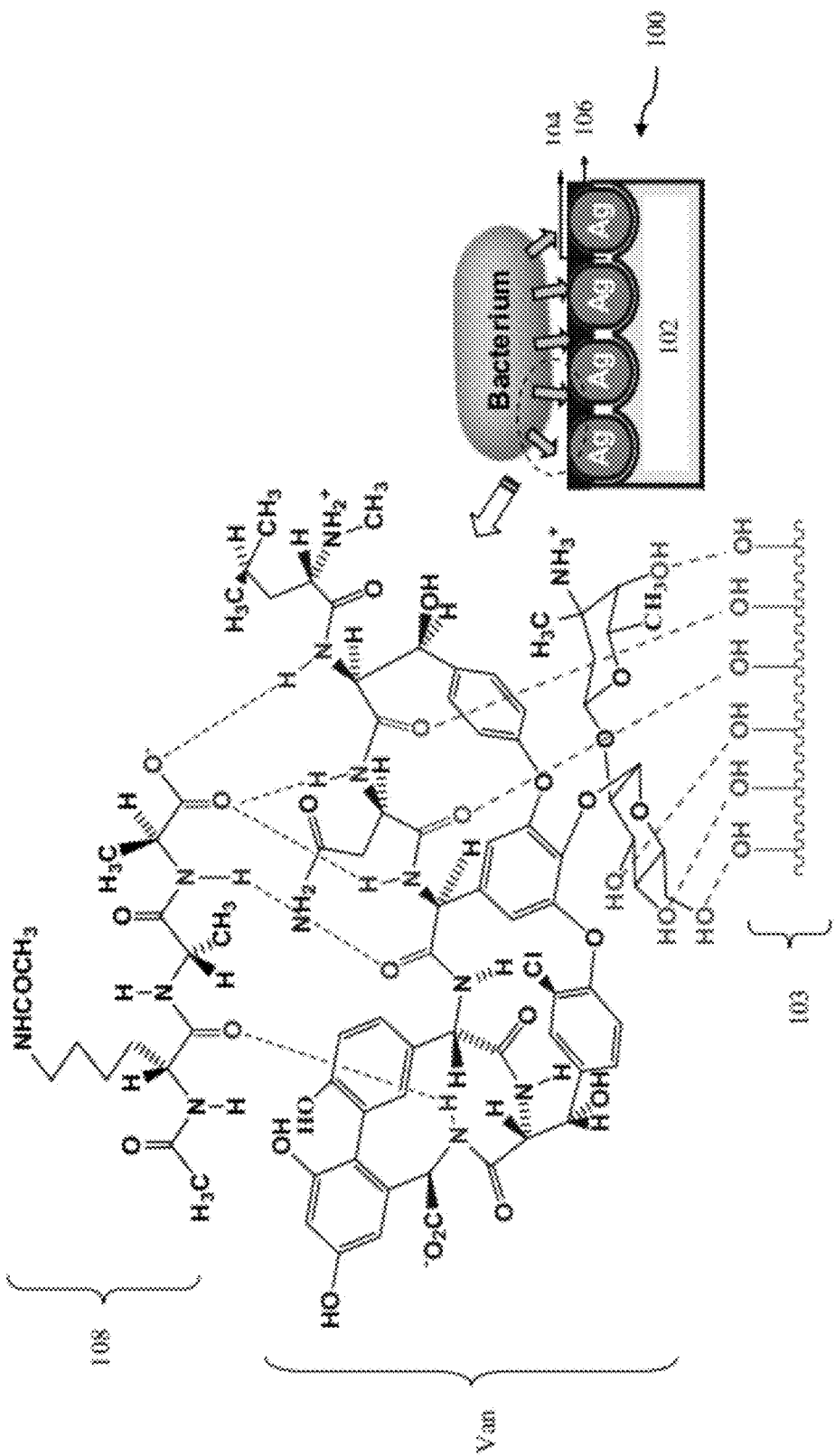
FIG. 1 is a schematic of a SERS active substrate used in this invention for capturing and detecting bacteria.

This invention relates to a SERS system and a method of using the system to capture and detect a target biomolecule such as a peptide on the cell wall of a bacterium. A schematic of the SERS system is illustrated in FIG. 1. More specifically, as shown in the right panel of FIG. 1, SERS system 100 includes a substrate 102 in which an array of wells 104 for holding metal nanoparticles (e.g., Ag nanoparticles) are formed, an array of nanoparticles partially embedded in the wells, and a layer of linking agent 106 covering the substrate and the nanoparticles. The linking agent 106 can bind to a biomolecule (e.g., protein, nucleic acid, polysaccharide, or lipid) or an organism (e.g., a bacterium, fungus or virus) via certain specific interactions (illustrated by gray arrows in FIG. 1). As such, when system 100 is brought into contact with a sample suspected of containing the target biomolecule or organism, it can capture the target biomolecule or organism. Binding of the target biomolecule or organism to the linking agent 106 would affect the chemical environment of the linking agent, leading to a change in the SERS spectrum of SERS system 100 (including SERS signals from both the linking agent and the biomolecule or organism). The SERS spectrum change can therefore indicate the presence of the target biomolecule or organism in the sample.

In one embodiment, the linking agent 106 in the SERS substrate of this invention is vancomycin (denoted as "Van" in the left panel of FIG. 1) and the target biomolecule is peptidoglycan or a certain fragment thereof such as D-Ala-D-Ala (denoted as "108" in FIG. 1) on the cell wall of Gram-positive and Gram-negative bacteria. As illustrated in the left panel of FIG. 1, vancomycin molecules bind to the terminal peptidoglycan, D-Ala-D-Ala, via hydrogen bonds, while vancomycin molecules also attach to the surface 103 of the SERS substrate 102 via hydrogen bonds.

Figure 2:
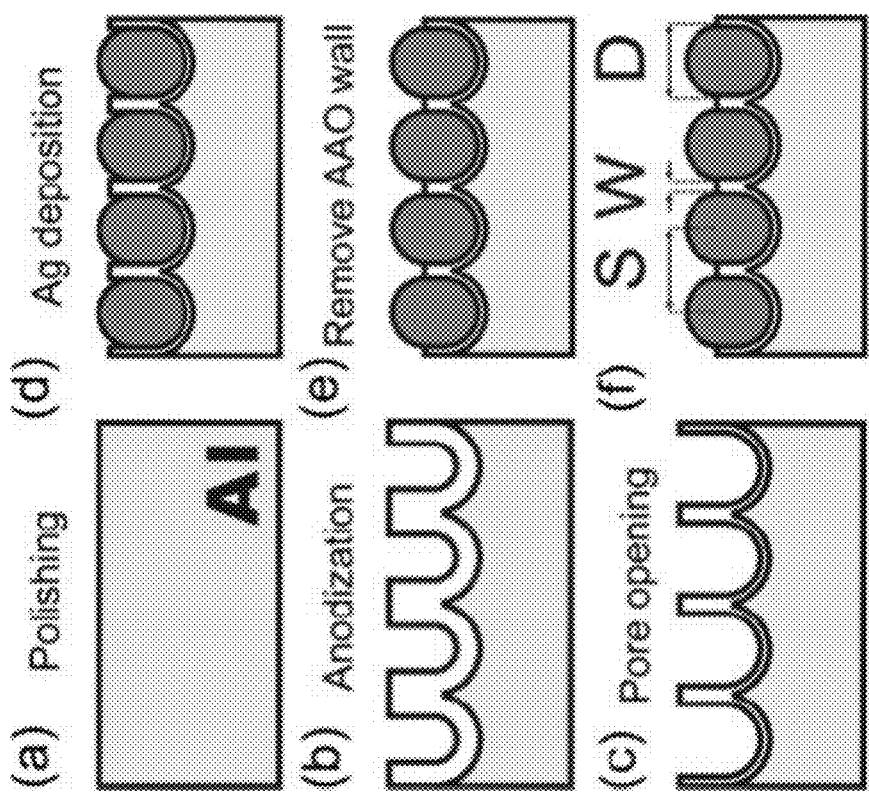
FIG. 2 is a schematic diagram showing the process for fabricating metal-filled porous anodic alumina substrates. In panel f: S, D, and W are the interparticle spacing, particle diameter, and inter-well/interparticle gap, respectively.

The substrate 102 as shown in FIG. 1 can be a metal substrate suitable for forming a nanometer-scale pattern of wells 104 via optical or e-beam lithography, electrochemical etching, or other etching methods. Examples of suitable metal include aluminum titanium, tantalum, niobium, tungsten, and zirconium. See, e.g., Wang et al., U.S. Pat. No. 7,453,565; Wang et al., *Adv. Mater.*, 18, 491-495 (2006); Liu, et al., *PLoS ONE*, 4, e5470-e5479 (2009); Singh et al., *ACS Nano*, 2 (12), 2453-2464 (2008); Shin & Lee, *Nano Lett.*, 8 (10), 3171-3173 (2008); and El-Sayed & Birss, *Nano Lett.*, 9 (4), 1350-1355 (2009). Preferably, aluminum is used as substrate 102. As illustrated by FIG. 2, an anodic aluminum oxide (AAO) template having arrays of wells or pores with a substantially uniform inter-well gap (denoted as "W" in panel f) is prepared and used for fabricating arrays of Ag nanoparticles separated by the uniform inter-well gaps. First, as shown in panels a and b, an aluminum substrate (e.g., an Al foil) is finely polished and then anodized to form self-organized, hexagonally close-packed AAO wells. Next, as illustrated in panel c, the wells/pores are further enlarged by, e.g., etching the substrate in 5% phosphoric acid for a selected duration. This etching process also allows the selective control of the gap between the Ag nanoparticles deposited in the wells, as the interparticle gap equals the inter-well gap. After depositing Ag nanoparticles of the desired length, the upper part of the AAO film is etched away in phosphoric acid to increase the area of exposed Ag. See panels d through f.

Figure 3:
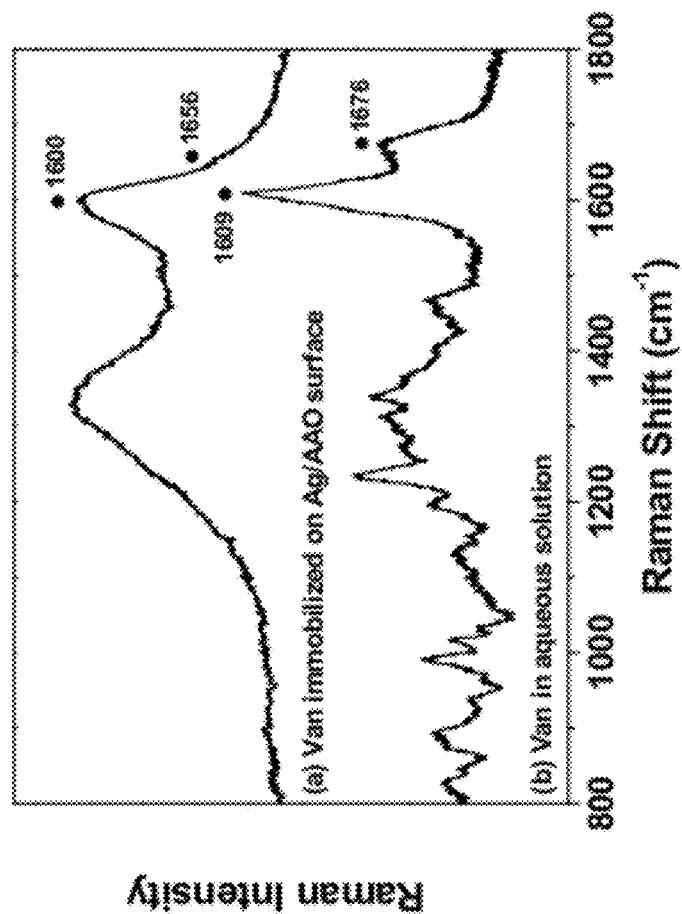
FIG. 3 illustrates Raman spectra of vancomycin in different forms.

After the substrate having an array of Ag nanoparticles partially embedded therein (i.e., "Ag/AAO substrate") is formed, the substrate is then placed into a solution containing a linking agent so that a layer of the linking agent can be coated onto the surface of the substrate and the exposed surfaces of the nanoparticles. In one example, Ag/AAO substrate is immersed in an aqueous solution of vancomycin hydrochloride with a concentration between 80 µM and 50 mM for a predetermined duration, thereby forming a vancomycin layer with a thickness between 5 nm and 100 nm. As illustrated by FIG. 1 and supported by FIG. 3, vancomycin binds to the Ag/AAO substrate via hydrogen bonds. As compared with the Raman spectra of vancomycin in solution form, i.e., profiles (b) in FIG. 3, both containing a few sharp peaks, the SERS spectrum of vancomycin on the Ag/AAO substrate i.e., profile (a) in FIG. 3, only contains two broad bands within the tested range, indicating that vancomycin molecules are randomly immobilized on the Ag/AAO substrate by hydrogen bonds between their C=O moieties and the hydroxyl moieties on the surface of the Ag/AAO substrate, which results in the broadening and the reduced intensity of the Raman peaks corresponding to C=O stretching mode. See Lee, *J. Raman Spectrosc.*, 28, 45-51 (1997). As the broadband background can be easily treated by a simple background subtraction routine in the data acquisition system, the lack of sharp peaks in the SERS spectrum of the vancomycin-functionalized Ag/AAO SERS substrate is unexpectedly superior to SERS substrates functionalized by other molecules exhibiting sharp Raman peaks which interfere with the SERS spectrum of the biomolecule to be detected. Also unexpectedly, upon vancomycin treatment, the Ag/AAO SERS substrate exhibits 700-fold increase in its capability to capture both Gram positive and negative bacteria as well as 5-fold enhancement in the SERS signal of the captured bacteria. See Example 2 below.

In other embodiments, vancomycin can bind to a nanoparticle-embedded substrate via covalent bonds (e.g., thiol-bonds). Unexpectedly, the bacteria capturing capability of a SERS substrate having vancomycin attached via hydrogen bonding is better than that via covalent bonding.

As mentioned above, the linking agent can interact with the nanoparticle-embedded substrate in a reversible manner so that the substrate can be reused by releasing the linking agents bound to the target biomolecule and depositing on the released substrate a fresh layer of linking agents. The release can be achieved by washing the target biomolecule-bound SERS system with a solution containing a compound that interacts more strongly with the linking agent than the substrate, at a suitable concentration, so as to produce a free nanoparticle-embedded substrate (no longer bound to linking agent 106). This free substrate can then be re-deposited with a layer of linking agents and re-used in a subsequent assay for detecting presence of a target molecule.

The SERS system of this invention can also be used to quantify a target biomolecule as follows. SERS system 100 is brought into contact with a solution containing a target biomolecule capable of binding to linking agent 106 at a predetermined concentration. The level of the SERS spectrum change (e.g., a Raman peak intensity change) of system 100 after exposure to the solution is determined. A standard curve is then prepared based on the concentrations of the target biomolecule (e.g., log values) versus the levels of spectrum changes caused thereby. SERS system 100 is then exposed to a sample containing the target biomolecule. The level of the SERS spectrum change is measured and the concentration of the target molecule is determined by comparing the spectrum change level with the standard curve.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference.

EXAMPLE 1

Fabrication of Vancomycin (Van)-Functionalized SERS Substrate

SERS-active Ag/AAO substrate containing arrays of Ag nanoparticles partially embedded in AAO nanowells, was fabricated according to the methods described in Wang et al., *Adv. Mater.*, 18, 491-495 (2006). More specifically, high-purity (99.99%) annealed aluminum foil was electropolished in a mixture of $HClO_4$ and $C_2H_5OH$ (volume ratio 1:5) until the root mean-square surface roughness of a typical 10 µm×10 µm area was 1 nm, as measured using an atomic force microscope operating in contact mode. The foil was then anodized in sulfuric acid (0.3 M) at 5° C. using a voltage in the 10-30 V range to obtain AAO substrates with arrays of self-organized wells with a diameter of a few nanometers to a few hundred nanometers ("nanowells"). The nanowells in the AAO substrate were then enlarged by etching the substrate in 5% phosphoric acid to increase the diameters of the nanowells. By carefully controlling the etching process, arrays of nanowells with 5±2 nm inter-well gap were achieved. An electrochemical plating procedure was then employed to grow Ag-nanoparticles into the AAO substrate. For growing Ag nanoparticles in the AAO nanowells, an alternating current (9 V) electrochemical plating procedure was employed using a mixture of silver nitrate (0.006 M) and magnesium sulfate (0.165 M) as the electrolyte solution with a pH value of 2, set by the addition of sulfuric acid. Since the deposition of Ag occurred primarily inside the nanowells, it was possible to avoid the merging of Ag nanoparticles by confining them inside the wells.

Next, an Ag/AAO SERS substrate (1×1 $cm^2$) produced by the method described above was immersed in an aqueous solution of vancomycin hydrochloride (Sigma, USA; with various concentrations of 80 µM-50 mM) for 1 hour, and then dried in the air for 12 hours to produce vancomycin-functionalized Ag/AAO SERS substrates with different coating thicknesses varying from 5 nm to 100 nm.

EXAMPLE 2

Characterizations of Vancomycin ("Van")-Functionalized SERS Substrate

*Escherichia coli* (*E. coli*, ATCC 11775) and *Lactobacillus plantarum* (*L. Plantarum*, ATCC 8014) were purchased from BCRC company in Taiwan. Three bacteria were cultivated for 16 h at 37° C. on Nutrient, MRS, and Brain Heart Infusion agar bases, respectively. After subculturing, single colonies were collected using sterile plastic inoculating loops. Bacteria were suspended in 5 mL specific broth, grown for an additional 14 hours then sub-cultured at $OD_{600}$~0.5, taken as the beginning of the exponential growth phase. They were then washed and centrifuged three times with water and re-suspended in water.

1 mL of bacteria solution (various concentrations: $10^4$~$10^9$ cfu/ml) was dropped onto a Van-functionalized SERS substrate placed in a well of a 24-well cell culture plate. Then, the bacteria were incubated at 37° C. under a 120 rpm shaking rate for 1 hour. Afterwards, the SERS substrate was washed with water 5 times before the Raman spectroscopy measurements were conducted.

Raman spectroscopy measurements were performed on a Raman microscopy (HR800, Jobin-Yvon) equipped with a HeNe laser at 632.8 nm (0.1 mW) and 50× objective lens. Individual single bacterium or clusters of bacteria were easily identified under this microscope system.

Raman signals were collected from the information-rich part of the spectrum between 400 and 1800 $cm^{-1}$ using 60 s acquisition time. The raw SERS readout datasets were processed and normalized to remove noises in the following three manners: (1) a median filter with noise estimation was applied to eliminate any sharp variations caused by cosmic rays; (2) a wavelet de-noising technique was used to smooth out high-frequency noise; and (3) iterative curve fitting to estimate and remove the background baseline due to the noise effect of environmental light.

Scanning electron microscopy (SEM) was performed on DualBeam™ FIB/SEM system (FEI Nova™ 600, USA).

Figure 4:
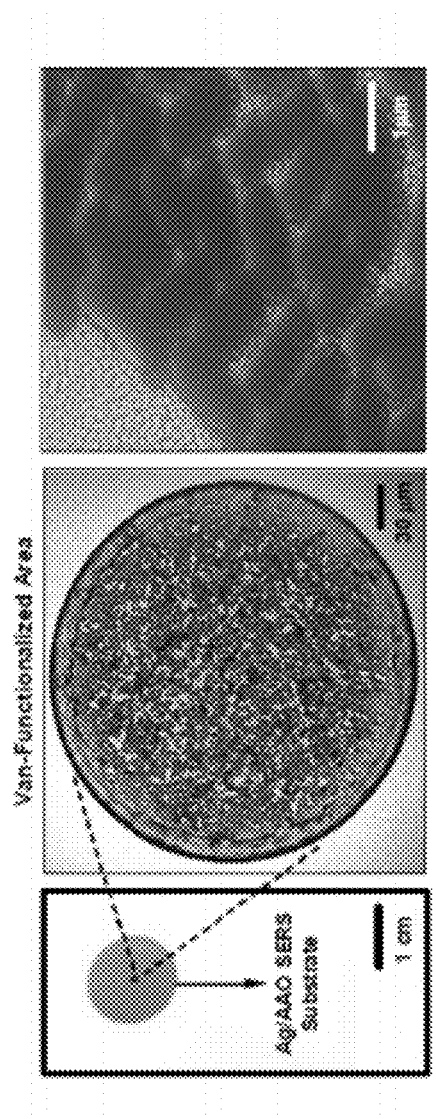
FIG. 4 illustrates the bacteria-capturing capability of a vancomycin-functionalized SERS substrate (coating solution: 10 mM vancomycin). Left panel: an optical image of a glass slide on which an Ag/AAO SERS substrate having a vancomycin-functionalized region (~300 μm in diameter) is placed; middle panel: a magnified view of vancomycin-functionalized region with the captured bacteria (*L. plantarum*); right panel: an SEM image of bacteria attached to the vancomycin-functionalized region.
Figure 5:
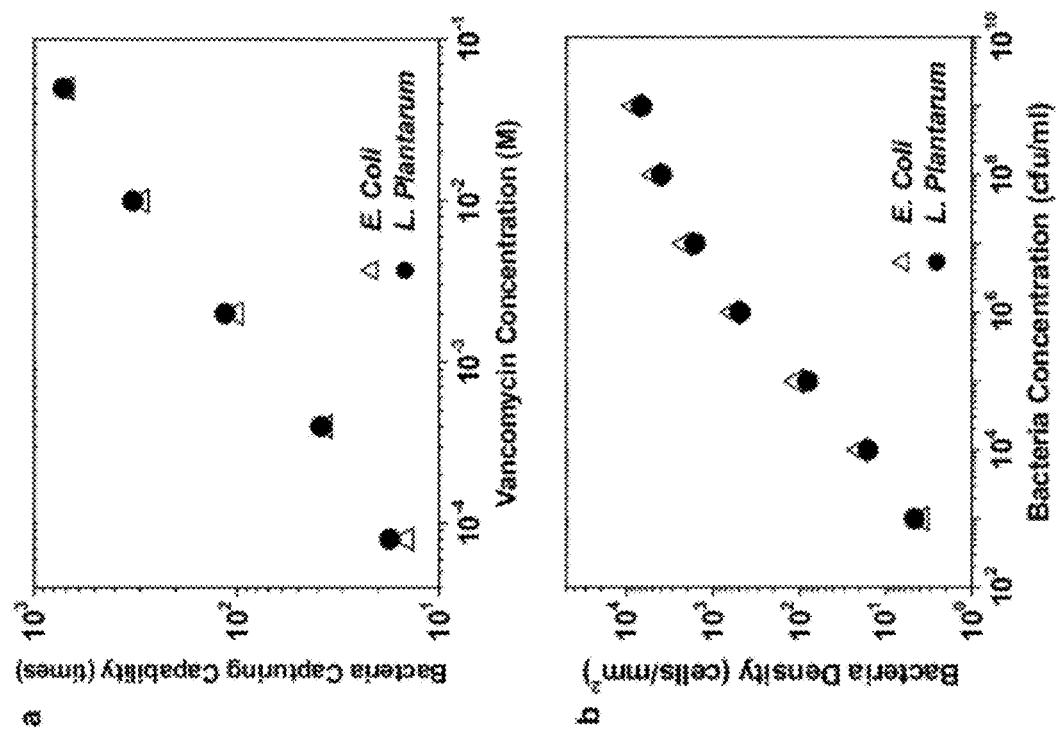

As shown in FIG. 4, *L. plantarum* (Gram-positive) bacteria were hedged and concentrated on a Van-functionalized region of a Ag/AAO SERS substrate, demonstrating the much stronger bacteria capturing capability of the Van-functionalized region than the Van-free Ag/AAO region. Quantitatively, FIG. 5a shows that the bacteria-capturing capability, defined as the ratio of the bacteria density (cells/$mm^2$) on a Van-functionalized substrate to the bacteria density on a Van-free Ag/AAO substrate, increased in a linear fashion as the vancomycin concentration of the coating solution increased for both *L. plantarum* and *E. coli* bacteria (Gram-negative). The bacteria-capturing capability increased by 700 times where the coating solution containing 50 mM vancomycin was used. Furthermore, the bacteria capturing capability also was evaluated under different bacteria seeding concentration ($10^3$~$10^9$ cfu/ml) on the Van-functionalized SERS substrates prepared from a 10 mM Van coating solution, as shown in FIG. 5b. The results indicate that bacteria density increases as bacteria seeding concentration increases. Also, the results indicate that the Van-functionalized SERS substrate can be sensitive to a bacteria seeding concentration as low as $10^2$ cfu/ml.

Figure 6:
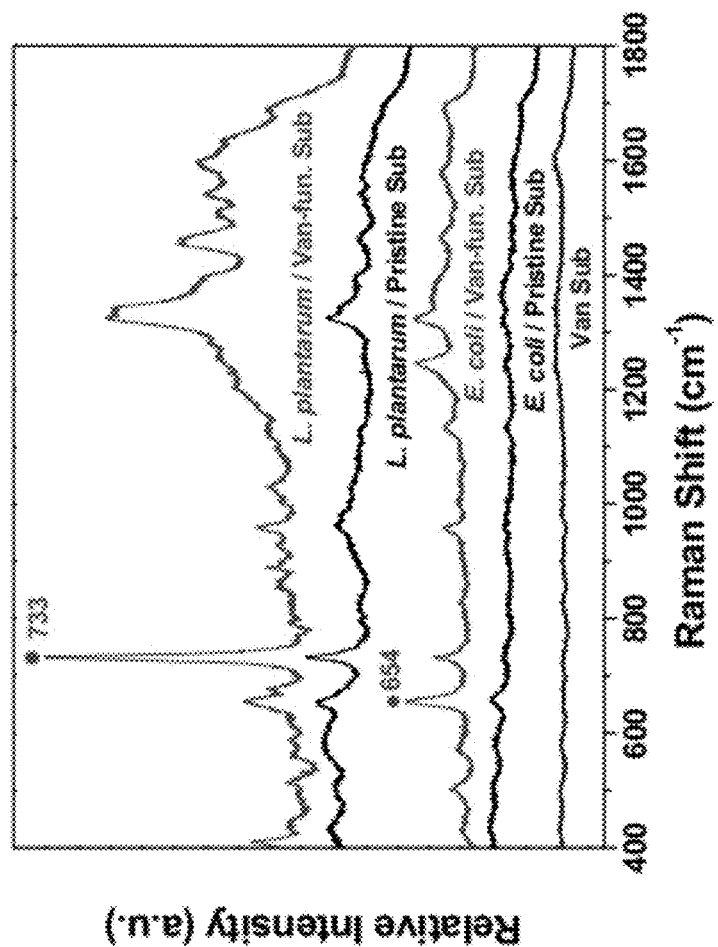
FIG. 6 illustrates relative SERS profiles (raw data after y-axis shift) from *E. coli* and *L. plantarum* bacteria on different substrates. A typical SERS of van-functionalized substrate is included for compoarison.

FIG. 6 illustrates the relative SERS profiles (raw data after y-axis shift) of *E. coli* and *L. plantarum* bacteria on different SERS substrates. Clearly, the Van-functionalized SERS substrates (denoted as "Van-fun. Sub" in FIG. 6) showed 4-5 times enhancement in the intensities of the major SERS peaks from the bacteria (733 $cm^{-1}$ peak from *L. plantarum* and 654 $cm^{-1}$ peak from *E. coli*) compared to that from Van-free Ag/AAO substrates (denoted as "Pristine Sub" in FIG. 6).

Figure 7:
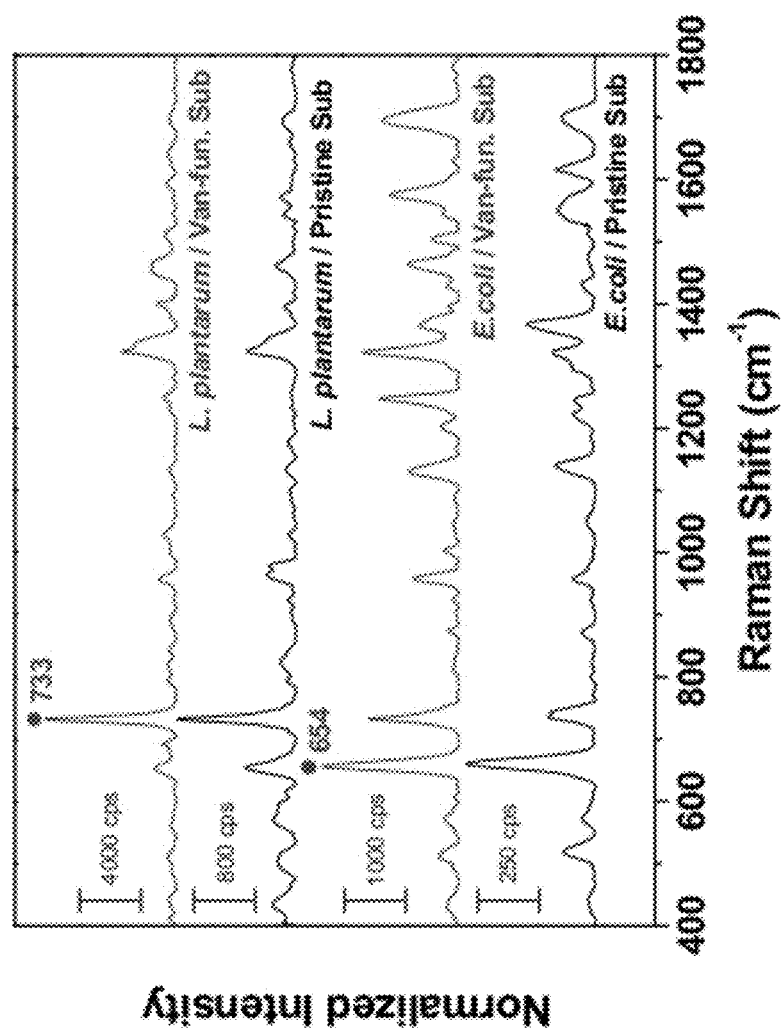
FIG. 7 illustrates normalized SERS profiles from *E. coli* and *L. plantarum* bacteria on different substrates. Scale bar exhibits the counts per seconds (cps) of Raman intensity respectively.

As shown in FIG. 7, the normalized SERS profile from the both bacteria on the Van-functionalized substrate (denoted as "Van-fun. Sub" in FIG. 7) exhibits no significant change in the positions and relative intensities of major SERS peaks, as compared to that from the Van-free Ag/AAO substrate (denoted as "Pristine Sub" in FIG. 7). However, some of secondary peaks in the bacteria cell wall become more obvious and shaper, especially in the negative bacteria with the thinner cell wall.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A surface-enhanced Raman spectroscopic (SERS) system for detecting a biomolecule, the system comprising:
    a substrate,
    an array of nanoparticles disposed on the substrate, each being partially embedded in the substrate and having a non-embedded surface, and
    a linking agent disposed on the non-embedded surface of each of the nanoparticles, interacting with the nanoparticle-embedded substrate via hydrogen bonds, wherein the linking agent, a glycopeptide antibiotic capable of binding to the biomolecule, forms a coating layer over the array of nanoparticles.

2. A surface-enhanced Raman spectroscopic (SERS) system for detecting a biomolecule, the system comprising:
    a substrate,
    an array of nanoparticles disposed on the substrate, each being partially embedded in the substrate and having a non-embedded surface, and
    a linking agent disposed on the non-embedded surface of each of the nanoparticles, interacting with the nanoparticle-embedded substrate via hydrogen bonds, wherein the biomolecule is a peptide on the cell wall of a bacterium; and the linking agent, a glycopeptide antibiotic capable of binding to the biomolecule, forms a coating layer over the array of nanoparticles, the coating layer having a thickness of 5-100 nm.

3. The SERS system of claim 2, wherein the glycopeptides antibiotic is selected from the group consisting of vacomycin, teicoplanin, ristocetin, telacancin, bleomycin, ramoplanin, chloroeremomycin, and decaplanin.

4. The SERS system of claim 1, wherein the linking agent is vancomycin.

5. The SERS system of claim 1, wherein the linking agent is reversibly attached to the non-embedded surface of each of the nanoparticles.

6. The SERS system of claim 1, wherein the linking agent is non-covalently attached to the non-embedded surface of each of the nanoparticles.

7. The SERS system of claim 1, wherein the linking agent has a molecular weight of not greater than 5 kDa.

8. The SERS system of claim 1, wherein the linking agent has a molecular weight of not greater than 2 kDa.

9. The SERS system of claim 1, wherein the coating layer has a thickness of 5-30 nm.

10. The SERS system of claim 1, wherein the substrate has a surface containing an array of wells having a uniform inter-well gap of 1-50 nm and the array of nanoparticles are disposed in the array of wells, each well containing one nanoparticle.

11. The SERS system of claim 10, wherein the wells are formed of an oxide selected from the group consisting of aluminum oxide, titanium oxide, tantalum oxide, and niobium oxide.

12. The SERS system of claim 10, wherein the wells are formed of aluminum oxide.

13. The SERS system of claim 10, wherein the uniform inter-well gap is less than 10 nm.

14. The SERS system of claim 1, wherein the non-embedded surface of each of the array of nanoparticles is formed of a metal selected from the group consisting of Ag, Au, and Cu.

15. The SERS system of claim 1, wherein each of the array of nanoparticles is formed of a metal selected from the group consisting of Ag, Au, and Cu.

16. A method for detecting presence of a biomolecule in a sample, the method comprising:
    providing a SERS system of claim 1,
    contacting the SERS system with a sample suspected of containing the biomolecule, and
    detecting a SERS spectrum change of the SERS system after the contacting step, wherein observation of a SERS spectrum change indicates presence of the biomolecule in the sample.

17. The method of claim 16, wherein the biomolecule is a peptide on the cell wall of a bacterium.

18. The method of claim 16, further comprising correlating a level of the SERS spectrum change with a concentration of the biomolecule in the sample.

19. The SERS system of claim 1, wherein the coating layer has a thickness of 5-100 nm.

20. The SERS system of claim 1, wherein the biomolecule is a peptide on the cell wall of a bacterium.

* * * * *